United States Patent [19]

Landman et al.

[11] 4,098,122
[45] Jul. 4, 1978

[54] TEMPERATURE PROBES

[75] Inventors: Brice Charles Landman, Figtree Heights; Granville Sykes, Keiraville; Thien Siung Yang, Mt. Ousley, all of Australia

[73] Assignee: The Broken Hill Propietary Company Limited, Melbourne, Australia

[21] Appl. No.: 710,308

[22] Filed: Jul. 30, 1976

[30] Foreign Application Priority Data

Aug. 5, 1975 [AU] Australia .................................. 2656

[51] Int. Cl.² ........................................... G01K 13/12
[52] U.S. Cl. .................................. 73/341; 73/421.5 A
[58] Field of Search ..................... 73/339 R, 341, 359, 73/421.5 R, 421.5 A, 23

[56] References Cited

U.S. PATENT DOCUMENTS

| 2,926,527 | 3/1960 | Crandall | 73/421.5 A |
|---|---|---|---|
| 3,085,435 | 4/1963 | Miscoe et al. | 73/421.5 A |
| 3,130,584 | 4/1964 | Kennedy | 73/341 |
| 3,240,069 | 3/1966 | Kennedy | 73/341 |
| 3,819,330 | 6/1974 | Creighton | 73/421.5 A |

Primary Examiner—Richard C. Queisser
Assistant Examiner—Stephen A. Kreitman
Attorney, Agent, or Firm—Larson, Taylor and Hinds

[57] ABSTRACT

The specification discloses a temperature/gas probe for use in a steel-making blast furnace comprising two tubes pivoted together at one end and having mounting means at their free ends adapted to co-operate with support structures within the walls of the furnace, the pivot means and the support means being such that the probe in use adopts a shallow V-configuration substantially corresponding to the profile of the burden in the furnace. Each tube supports a plurality of thermocouples which extend from the tube in spaced relation along the length of the tube. The thermocouples are housed in tubes within the tubes, said thermocouple housing tubes extending to the free ends of the probe tubes to facilitate easy replacement of the thermocouples as they wear out. The thermocouples are connected to a recording apparatus which provides a temperature profile print-out at any desired time. The thermocouple housing tubes may also be used to collect gas samples from the furnace.

In a modification, a single tube similar to one of the two tubes referred to above is supported by similar support means within the wall of the furnace, said tube adopting a disposition corresponding to the profile of half of the burden in the furnace. This modification is suitable only for small furnaces not having a high top pressure.

7 Claims, 7 Drawing Figures

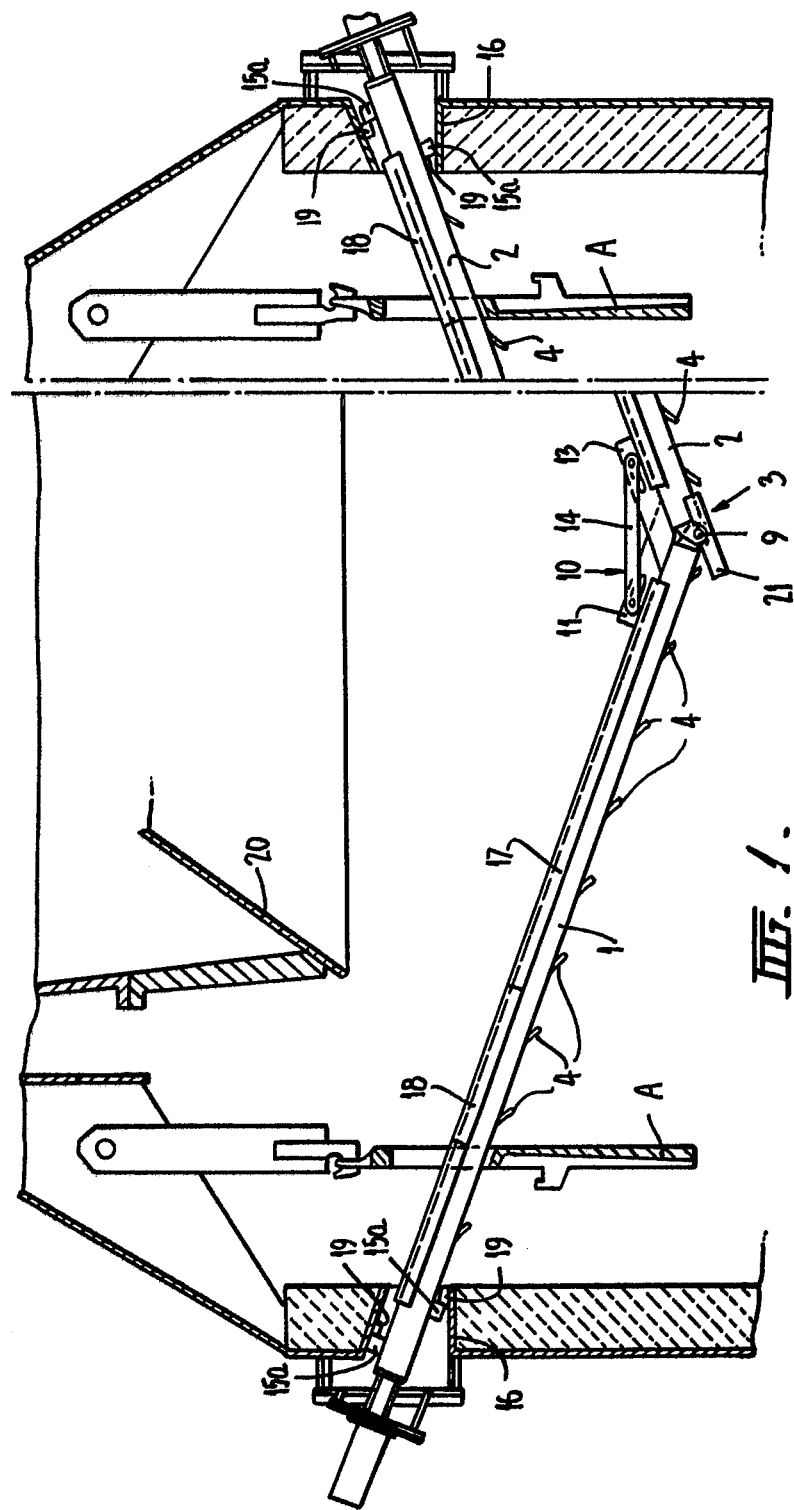

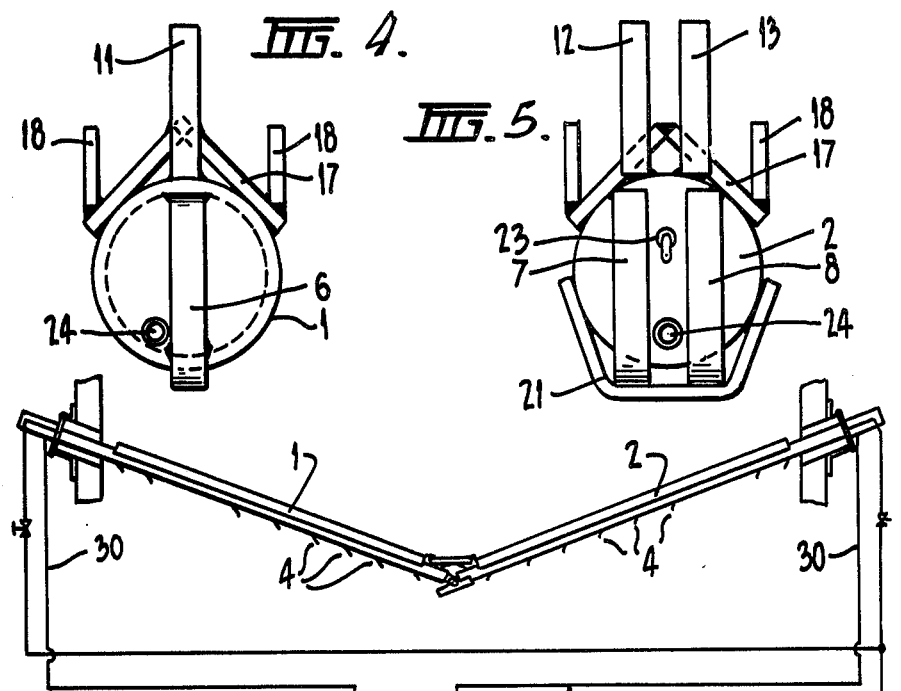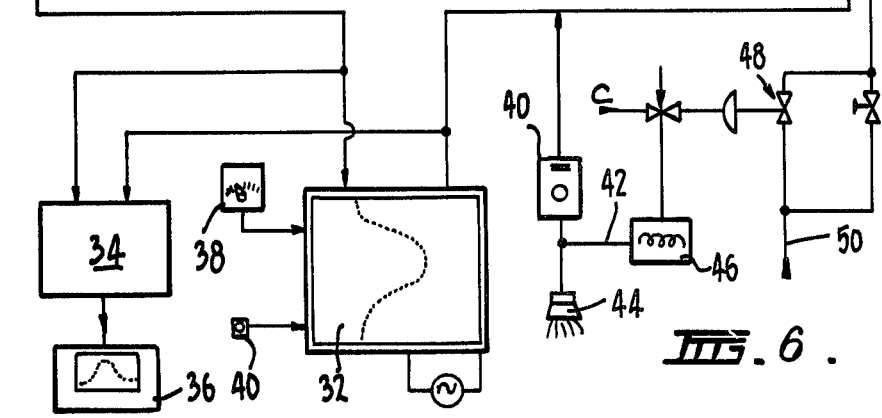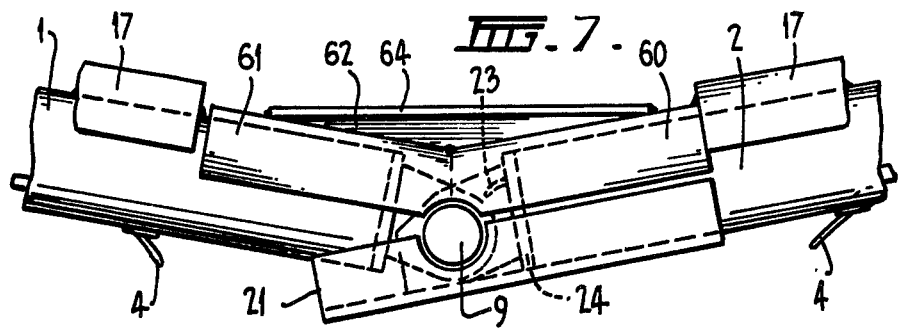

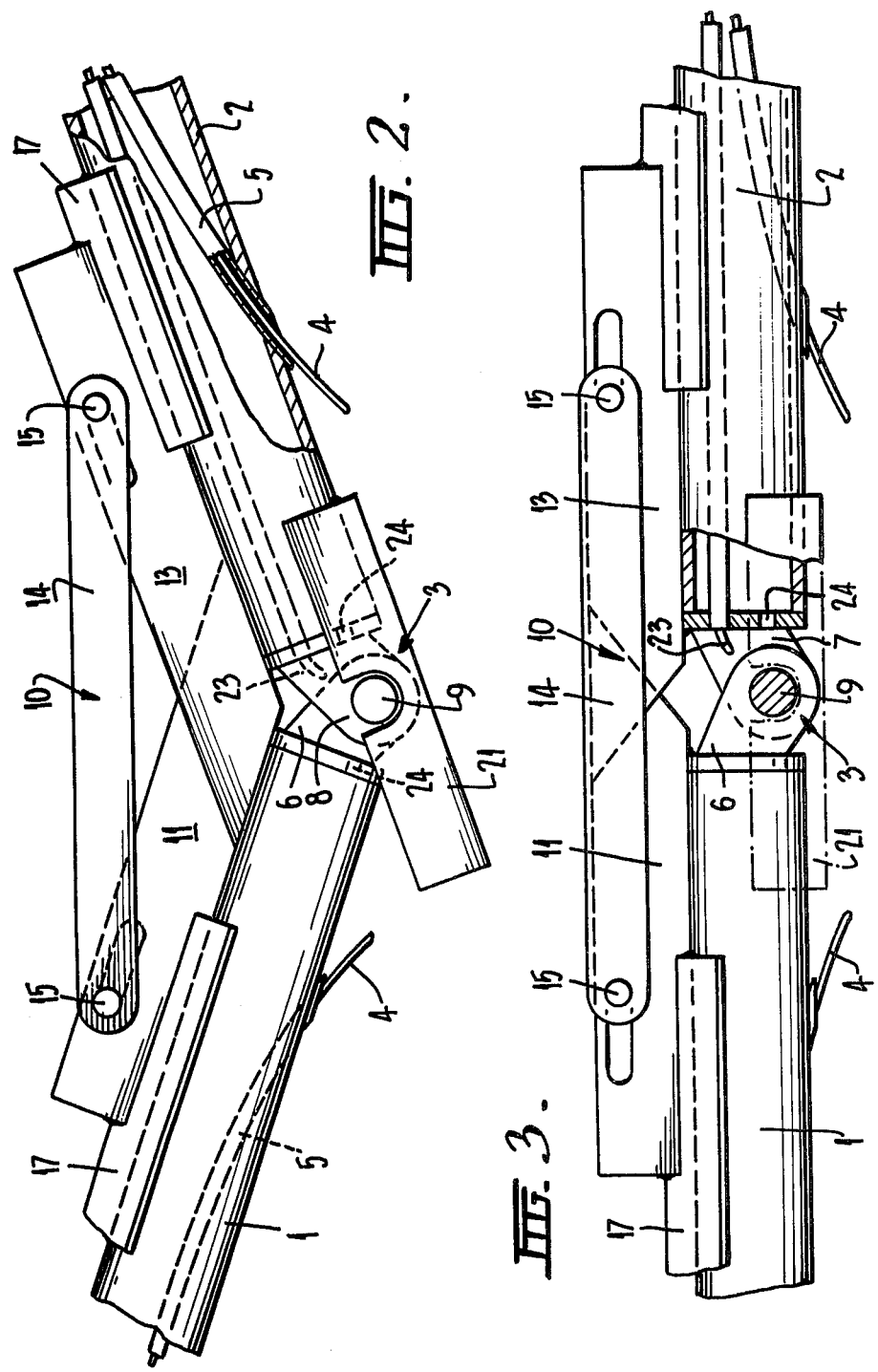

TEMPERATURE PROBES

This invention relates to improvements in probes to be used for monitoring physical/chemical properties, such as temperature and chemical properties of gases, in hostile environments such as those experienced in blast furnaces. The invention is not restricted to this use, but for convenience the following description is directed to this application of the invention.

In operating a blast furnace it is desirable to know the profile of the temperature across the burden at about its midpoint in the furnace. There are available various kinds of temperature probes that are capable of insertion into the burden through the wall of the furnace to take temperature measurements across one-half of the material but these are extremely expensive and have substantial servicing requirements. Furthermore, such probes cannot continually monitor the temperature profile as they must be withdrawn shortly after insertion.

In an endeavour to overcome the high cost, it has been proposed to provide a similar probe which is inserted into and withdrawn from the furnace through a valved opening in the wall of the furnace above the burden by means of an hydraulic or like mechanism. Temperature measurements taken in this way, while not being as informative as the measurements taken within the material, arwe nevertheless useful. However, such devices are still relatively expensive and still have demanding servicing requirements.

Both of the above prior art devices require the building of substantial support structures on the side of the furnace. Such structures add to the capital cost of the device and are generally inconvenient.

The main object of the invention is to provide a commercially acceptable alternative which is less costly than the first arrangement described above, and is at least less demanding as regards servicing than the second arrangement described.

The invention provides an improved probe for monitoring physical and/or chemical properties, such as temperature and chemical composition, of a material in a hostile environment, comprising an elongate member supporting a plurality of sensing and/or collecting devices spaced along its length, means for securing one end of said member to a container for said material, said securing means and said elongate member being constructed and arranged so that in use the elongate member adopts a disposition which substantially corresponds to at least one-half of the configuration of the profile of the material in the container, whereby the member is at about the same distance from the surface of the material along its length.

For containers having large dimensions, e.g. greater than 8m across, the elongate member has its opposite ends adapted to be secured to said container, said elongate member and said securing means being such that said elongate member adopts a disposition in use which substantially corresponds to the profile of the material in the container.

In a preferred form of the invention as applied to a blast furnace, in which the material profile is substantially a shallow V-configuration, the probe comprises two hollow support members, such as tubes, pivoted together at one end and adapted to be mounted at their free ends in support structures secured within the walls of the furnace at diametrically opposed positions, and means extending between said pivoted ends and engaging same to prevent pivotal movement beyond said shallow V-configuration. In the working position the two tubes are held in a shallow V-configuration just above the surface of the furnace burden. At least one of the support tubes houses thermocouple or the like guide tubes extending from a plurality of positions, spaced along the length of the tube, where they pass through its wall, to the free end of the support tube. This arrangement facilitates easy replacement of the thermocouples as they wear out. Furthermore, the guide tubes may be used for the extraction of gases for analysis so that the probe may function both as a temperature probe and/or as a gas sampler.

The hollow support tubes are preferably interconnected by a linkage or brace member arrangement which enables the tubes to be held in a straight line configuration for fitting to the furnace and which prevents the tubes from pivoting further than the desired V-configuration when released into the working position.

A particularly preferred arrangement will now be described with reference to the accompanying drawings in which:

FIG. 1 is a side elevation of the temperature probe arrangement installed in a blast furnace;

FIG. 2 is a partly fragmentary enlarged elevation of one form of joint between the probe tubes in the installed condition shown in FIG. 1;

FIG. 3 is an elevation similar to FIG. 2 but shows the joint in the condition it assumes during installation of the probe;

FIGS. 4 and 5 are end views of the two tubes at the 'joint' end;

FIG. 6 is a schematic system diagram showing the probe with its associated recording, display and alarm instruments, and FIG. 7 shows an alternative for the joint between the two tubes of the probe.

Referring firstly to FIG. 1, the temperature probe comprises two stainless steel tubes 1 and 2 connected at their inner ends by a pivotal joint 3 (FIG. 2). Each tube 1, 2 supports a plurality of shielded thermocouple devices 4 at the positions indicated. As shown in more detail in FIG. 2 each thermocouple 4 is housed in its own guide tube 5 which passes through and is secured within an opening in the wall of the tubes 1 or 2. The other ends of the guide tubes 5 project through an array of holes in an end plate (not shown) closing the outer ends of tubes 1 and 2. This arrangement facilitates quick and convenient assembly and replacement of the thermocouples 4 from the outer ends of the tubes 1 and 2.

The pivotal joint 3 between the tubes 1 and 2 comprises a lug 6 (FIGS. 2, 4 and 5) secured centrally to an end plate closing the tube 1 and two spaced lugs 7 and 8 secured to an end plate closing tube 2. The lugs 6, 7 and 8 are formed with aligned apertures which receive a pivot pin 9.

A heat shield 21 is welded to the end of the tube 2 and extends past the end of the tube 2 to protect the pivotal joint 3 from direct hot gas or flame impingement.

The two tubes 1 and 2 are also interconnected by a sliding joint linkage 10 comprising three elongate plates 11, 12 and 13 welded to the tubes 1 and 2 as shown in FIGS. 3 and 4 and having a pair of links 14 joined by pins 15 passing through slots in the plates 11, 12 and 13.

This linkage 10 enables the probe tubes 1 and 2 to be held in a straight line, as shown in FIG. 3, for installation purposes and restricts the pivotal movement of the joint 3 to the required degree. The locking of the tubes in the operative position shown in FIG. 1 is further assisted by the provision of angled ends on the plates 11, 12 and 13 which engage the other tubes 1 and 2 when these have reached the desired angular disposition.

The free end of each tube 1, 2 has stop members 15a secured thereto and these co-operate with box structures 16 which are inserted into the brick lining of the furnace through holes cut in the outer wall of the furnace.

The stop members 15a at each outer end interlock with stop members 19 on the box structure 16 when the tubes 1 and 2 are lowered to the desired angular disposition.

The tubes 1 and 2 are reinforced by plates 17 arranged as shown in FIGS. 1 and 4 and each tube has an impact box structure 18 (FIG. 4) along that section of each tube 1, 2 that is subjected to falling materials entering the furnace through the charging bell 20. The structure 18 fills with material and reduces the amount of wear caused by the charging operation.

An additional thermocouple 23 passes through the end plate closing tube 2 and is located adjacent to the upper part of the pivotal joint 3 to sense when the linkage is subjected to excessively high temperatures of more than 500° C.

A steam injection opening 24 is provided in each of the end plates closing the inner ends of the tubes 1 and 2. Steam pipes (not shown) are connected to the end plates in the outer ends of the tubes 1 and 2 for connection to a steam supply line to be described later. Cooling steam is injected through the pipes into the tubes 1 and 2 and passes through the openings 24 to the pivotal joint 3. The thermocouple is connected to a control system, to be described later, which automatically causes injection of steam when a predetermined temperature is exceeded. Alternatively, steam injection may be performed manually and the thermocouple is in this case connected to an alarm generating circuit so that the operator is made aware that the predetermined temperature has been exceeded.

The temperature probe is fitted to the furnace in the following way. Holes are cut through the outer wall of the furnace and the brick lining knocked out in this region to facilitate the fitting of the box structures 16. Suitable apertures are cut in the shielding apron A. A winch line is passed through the furnace and connected to a winch on the left side of the furnace in FIG. 1. A suitable supporting structure (not shown) is formed on the existing furnace framework for supporting the probe while it is being inserted into the furnace. The winch line is secured to one end of the probe and the probe is drawn through the furnace while maintaining it under longitudinal tension to prevent pivotal movement of the joint 3 from the position shown in FIG. 3. When the probe reaches the other box structure 16, the tension is released and the probe is lowered into the working position shown in FIG. 1.

In use, the probe adopts a configuration which closely resembles the profile of the material in the furnace so that the probe is substantially parallel to the material throughout its length. Thus each of the thermocouples 4 effectively monitors the temperature of gas stream immediately above the burden material while the furnace is in operation.

The thermocouples 4 may be connected to any suitable recording device to provide either a permanent record of the temperature profile or a visual display on a cathode ray tube. These two alternatives, as well as the schematic circuitry of the steam injection system, are shown in FIG. 6.

In the arrangements shown in FIG. 6, the thermocouples 4 and 23 are connected via multicore cables 30 to a multipoint recorder 32 or to computer system 34 having a cathode ray tube display 36. The recorder 32 may be a Leeds and Northrup "Speedomax H" having an Eagle synchronous motor timer 38 and a pushbutton 40 connected thereto via relays (not shown). The timer 38 may be set to produce a temperature profile print at predetermined intervals or an instantaneous profile print provided by pushing button 40.

The thermocouple 23 is connected to an alarm tripping circuit 44. The tripping circuit 42 is also connected to a solenoid valve 46 which opens and closes, by means of compressed air C, steam control valve 48 in the steam supply line 50. Thus, when the circuit 40 is tripped by the thermocouple 23 sensing excessive temperatures, steam is supplied via line 50 and passes through the holes 24 to cool joint 3. In the arrangement shown, it has been found that a steam injection rate of the order of 20 kg/min is adequate and has no deleterious effects on the blast furnace operation. However, under normal furnace operation temperatures are such that steam is not required.

Due to the extreme temperatures and the reactive atmosphere, the thermocouples require occasional replacement but this is easily achieved as described above. When the tubes eventually break down a new probe is positioned in the furnace to eventually melt away.

A probe in accordance with the above description was initially installed in the Port Kembla No. 5 Blast Furnace and failed after seven months of service. A further probe was installed in Port Kembla No. 3 Blast Furnace in September 1974 and was lost in May 1975. Another probe was installed in the Port Kembla No. 4 Blast Furnace in May 1975 and is still in operation. Hence, it is believed that probes embodying the invention will have a life of between six and eighteen months depending on the severity of furnace operation. As this probe is a tool to aid furnace operators in reducing the severity of furnace operation, its life will increase as the furnace operation improves. It is anticipated that when the furnace operation has been considerably improved with the aid of this probe, the life of the probe may increase to 2 years or more.

Thus, in view of the lower cost of the probe compared with the prior art, it is believed that it provides an acceptable commercial alternative, especially in the light of its superior operation compared to the burden probes described earlier.

The probe described above may also be used to withdraw gas samples and for this purpose the thermocouple guide tubes are connected to a gas sampler for external analysis of the gas constituents. This can be done either continuously, with periodic steam purge, or as required. The results may be either manually or automatically plotted to give the distribution profiles of blast furnace gas constituents such as CO (Carbon Monoxide) $CO_2$ (Carbon Dioxide) $H_2$ (Hydrogen) and $CH_4$ (Methane).

The modified joint shown in FIG. 7 of the drawings operates in a manner similar to the first embodiment and like reference numerals denote like parts. In this embodiment the linkage arrangement is replaced by a pair of half-round sections 60 and 61 welded together and braced at the desired angle by means of a gusset 62 and a top plate 64 welded to the sections 60, 61. Section 60 is securely welded to tube 2 so that when the tube is at the desired inclination, the section 61 serves as a stop and prevents further pivotal movement.

The advantages of the present system may be achieved in the use of small furnaces (less than 8m in diameter without high top pressure) by means of a probe comprising a single tube of construction and length similar to one of the tubes described above. In such furnaces it is possible to do away with the centre joint since the tube lengths in question are sufficiently strong to withstand the impact of the smaller quantities of burden introduced into the furnace. A half-probe of this type has been successfully tested in the Port Kembla No. 2 furnace for about eighteen months.

It will be appreciated that more than one such half-probe may be used. For example two probes may be arranged in a manner similar to the above embodiment or four probes spaced by 90° may be positioned in the furnace.

Of course it will be appreciated that for larger furnaces, one of the tubes need not carry thermocouples and may simply be there to support the other tube in the required orientation. However, the additional information is useful and therefore is better recorded than not. Nevertheless, the invention is equally applicable when only one tube collects the desired data.

While the above description refers to the use of steam as the coolant and purge, it will be appreciated that other suitable gaseous materials may be used for these purposes.

We claim:

1. An improved probe for monitoring physical and/or chemical properties such as temperature and chemical composition of a material in a blast furnace in which the material profile is substantially a shallow V-configuration, comprising an elongate probe member supporting a plurality of sensing and/or collecting devices spaced along its length, said elongate probe member comprising two hollow support members pivoted together at one end and adapted to be mounted at their free ends, means for securing said free ends of said hollow support members to said blast furnace at diametrically opposed positions, said securing means and said elongate member being constructed and arranged so that, in use, said elongate member adopts a position which substantially corresponds to the shallow V-configuration of the profile of the material in the blast furnace whereby the member is at about the same distance from the surface of the material along its length, and means extending between said pivoted ends and engaging same to prevent pivotal movement beyond an angle in which the tube adopts a disposition generally corresponding to said shallow V-configuration.

2. The probe of claim 1, wherein at least one of the support members is a tube which houses thermocouple or the like guide tubes extending from a plurality of positions, spaced along the length of the tube, where they pass through its wall to the free end of the support tube, to the outer ends of the tubes.

3. The probe of claim 1, wherein the means extending between said pivoted ends comprises a link member having connecting pins passing through slotted holes in means rigidly secured to said tubes, said link member and said slots being of such lengths that the tubes may be held in a straight line configuration for installation to the container while preventing pivotal movement beyond the desired V-configuration.

4. The probe of claim 1, wherein the means extending between said pivoted ends comprises a brace member having a shallow V-configuration generally corresponding to said profile, one section of said V-configuration being rigidly secured to one of said tubes with the other section overlying the other tube whereby the tubes may be held in a straight line configuration for installation to the container while preventing pivotal movement beyond the desired V-configuration.

5. The probe of claim 1, further comprising a heat shield extending from one tube to cover the pivotal connection from beneath.

6. The probe of claim 1, further comprising steam supply pipes opening into the tubes and holes at the ends of the tubes positioned to direct steam into the pivotal connection, and a further thermocouple exposed to the heat at the pivotal connection for detecting when the temperature at this position is excessive.

7. A system for monitoring physical and/or chemical properties of materials in a hostile environment comprising a fixed elongate probe having its inner end extending into a blast furnace for said material, means supporting and securing the outer end of said elongate probe to said blast furnace whereby the probe is supported in said blast furnace solely at the point of securement to said blast furnace, said elongate probe carrying first means for detecting the property and/or collecting material from said blast furnace, said first means being spaced along the length of said probe for coupling said first means to apparatus for displaying information related to the properties detected by said first means whereby an instantaneous profile of said properties of said material along the length of said probe is displayed, said elongate probe member comprising two hollow support members pivoted together at one end and adapted to be mounted at their free ends, means for securing said free ends of said hollow support members to said blast furnace at diametrically opposed positions, said securing means and said elongate member being constructed and arranged so that, in use, said elongate member adopts a position which substantially corresponds to the shallow V-configuration of the profile of the material in the blast furnace whereby the member is at about the same distance from the surface of the material along its length, and means extending between said pivoted ends and engaging same to prevent pivotal movement beyond an angle in which the tube adopts a disposition generally corresponding to said shallow V-configuration.

* * * * *